(12) United States Patent
Fan et al.

(10) Patent No.: US 8,241,917 B2
(45) Date of Patent: Aug. 14, 2012

(54) ISOTOPE-DOPED NANO-MATERIAL, METHOD FOR MAKING THE SAME, AND LABELING METHOD USING THE SAME

(75) Inventors: Shou-Shan Fan, Beijing (CN); Liang Liu, Beijing (CN); Kai-Li Jiang, Beijing (CN)

(73) Assignees: Tsinghua University, Beijing (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 15 days.

(21) Appl. No.: 12/794,356

(22) Filed: Jun. 4, 2010

(65) Prior Publication Data
US 2011/0159604 A1    Jun. 30, 2011

(30) Foreign Application Priority Data

Dec. 31, 2009   (CN) .......................... 2009 1 0239661

(51) Int. Cl.
*G01N 33/00* (2006.01)
*C01B 31/02* (2006.01)
*C01B 31/00* (2006.01)

(52) U.S. Cl. .......................... 436/145; 427/585; 427/446
(58) Field of Classification Search .................. 436/145; 428/401, 403, 34.1; 427/585, 446
See application file for complete search history.

(56) References Cited

U.S. PATENT DOCUMENTS

| | | |
|---|---|---|
| 4,338,520 A | 7/1982 | Stewart |
| 4,427,884 A | 1/1984 | Anbar et al. |
| 4,900,830 A | 2/1990 | Fisher et al. |
| 5,753,088 A | 5/1998 | Olk |
| 5,773,834 A | 6/1998 | Yamamoto et al. |
| 6,139,919 A | 10/2000 | Eklund et al. |
| 6,183,714 B1 | 2/2001 | Smalley et al. |
| 6,232,706 B1 | 5/2001 | Dai et al. |
| 7,029,751 B2 | 4/2006 | Fan et al. |

OTHER PUBLICATIONS

Katz, E. et al., Biomolecule-Functionalized Carbon Nanotubes: Applications in Nanobioelectronics, 2004, ChemPhysChem, 5, pp. 1084-1104.*
Sumio Iijima, Helical Microtubules of Graphitic Carbon, Nature, Nov. 7, 1991, 354,6348 Academic Research Library, GB.
W. Z. Li, S. S. Xie, L. X. Qian, B. H. Chang, B. S. Zou, W. Y. Zhou, R, A, Zhao, G. Wang. Large-scale Synthesis of Aligned Carbon Nanotubes, Science, Dec. 6, 1996, vol. 274, 1701-1703. US.
Liu, et al. Isotope Labelling of Carbon Nanotubes and Formation of 12C-13C Nanotube Junctions, J. Am. Chem. Soc.2001; 123; 11502-11503.
Fan, et al., Monitoring the growth of carbon nanotubes by carbon isotope labelling, Nanotechnology 2003; 14: 1118-1123.
Zidan et al, "Doped Carbon Nanotubes for Hydrogen Storage", US DOE Hydrogen Program Review, 2002.

(Continued)

*Primary Examiner* — Christine T Mui
(74) *Attorney, Agent, or Firm* — Altis Law Group, Inc.

(57) ABSTRACT

An isotope-doped nano-structure of an element is provided. The isotope-doped nano-structure includes at least one isotope-doped nano-structure segment having at least two isotopes of the element, and the at least two isotopes of the element are mixed uniformly in a certain proportion. The present disclosure also provides a method for making the isotope-doped nano-structures, and a labeling method using the isotope-doped nano-structures.

14 Claims, 5 Drawing Sheets

OTHER PUBLICATIONS

Chen et al. "Chemically Doped Double-Walled Carbon Nanotubes: Cylindrical Molecular Capacitors", Phys. Rev. Letters, vol. 90, No. 25, 257403, Jun. 2003.

T. W. Ebbesen & P. M. Ajayan, Large-scale synthesis of carbon nanotubes, Nature, Jul. 16, 1992, 358, 6383, Academic Research Library, GB.

Zhang, et al., Heterogeneous growth of B-C-N nanotubes by laser ablation, Chemical Physics Letters 1997; 279; 264-269.

Maruyama et al. "Effect of Carbon Isotope Abundance on thermal conductivity and Raman scattering of single-walled carbon nanotubes", ISMME 2003-109(Dec. 2003).

* cited by examiner providing a plurality of different types of unlabeled structures and a plurality of different kinds of isotope-doped nano-structures of an element having certain Raman spectrum eigenvalues, each kind of isotope-doped nano-structure comprising at least one isotope-doped nano-structure segment having at least two isotopes of the element, and the at least two isotopes of the element being mixed uniformly in a predetermined mass proportion

↓ implanting one kind of the isotope-doped nano-structures of the element in one type of the unlabeled structures

↓ measuring the Raman spectrum eigenvalues of isotope-doped nano-structures of the element planted in the unlabeled structures via Raman spectroscopy

↓ distinguishing the unlabeled structures in accordance with the measured Raman spectrum eigenvalues

FIG. 5

ISOTOPE-DOPED NANO-MATERIAL, METHOD FOR MAKING THE SAME, AND LABELING METHOD USING THE SAME

RELATED APPLICATIONS

This application claims all benefits accruing under 35 U.S.C. §119 from China Patent Application No. 200910239661.9, filed on Dec. 31, 2009 in the China Intellectual Property Office.

BACKGROUND

1. Technical Field

The present disclosure relates to nano-materials, methods for making the same, and labeling methods using the same and, particularly, to an isotope-doped nano-structure of an element, a method for making the same, and a labeling method using the same.

2. Discussion of Related Art

Isotope labeling is a powerful tool in the study of nano-material growth mechanisms and in nano-sized isotope junction synthesis. Methods of isotope labeling use reactants containing different isotopes of a special element (usually light elements such as carbon, boron, nitrogen and oxygen), which are fed in designated concentrations (pure or mixed) and sequences into a nano-material synthesis process to provide in situ isotope labeling of nano-materials.

A typical example is shown and discussed in U.S. Pat. No. 7,029,751B2, entitled, "ISOTOPE-DOPED CARBON NANOTUBE AND METHOD AND APPARATUS FOR FORMING THE SAME," issued to Fan, et al. on Apr. 18, 2006. This patent discloses an isotope-doped carbon nanotube and method for making the same. The isotope-doped carbon nanotube includes a plurality of carbon nanotube segments, and each of the carbon nanotube segments is composed of a single carbon isotope. There are three naturally occurring carbon isotopes, which are used for labeling. However, the number of labels is limited by the number of combinations of the three isotopes, which limits isotopic labeling.

What is needed, therefore, is an isotope-doped nano-structure of an element, a method for making the same, and a labeling method using the same, the isotope-doped nano-structure of the element can be used for labeling different kinds of substances.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

FIG. 5 is a flow chart of a labeling method using isotope-doped carbon nanotubes.

DETAILED DESCRIPTION

Figure 1:
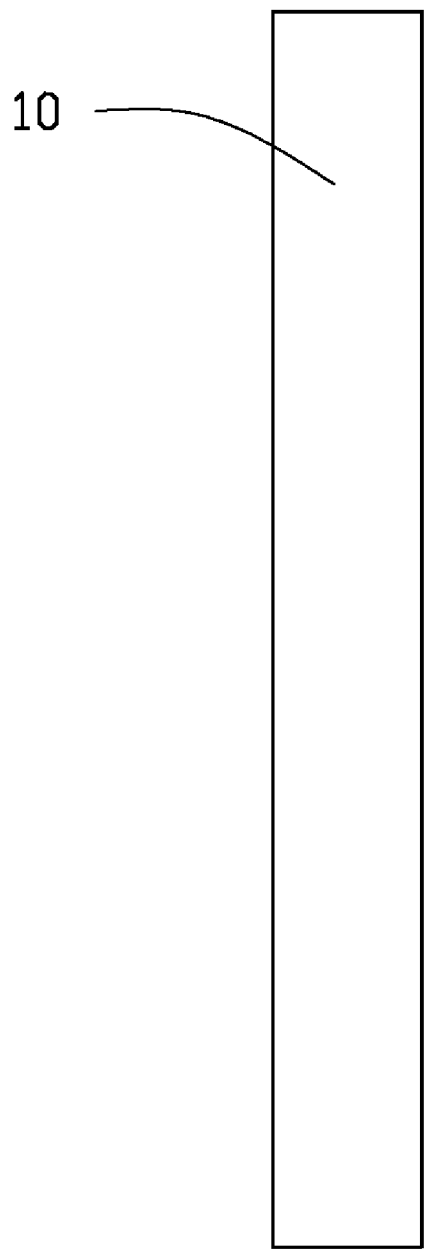
FIG. 1 is a schematic view of one embodiment of an isotope-doped carbon nanotube.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

An isotope-doped nano-structure of an element is disclosed. The isotope-doped nano-structure includes at least one isotope-doped nano-structure segment having at least two isotopes of the element, and the at least two isotopes of the element are mixed uniformly according to a certain mass proportion.

Specifically, when the isotope-doped nano-structure is composed of only one isotope-doped nano-structure segment, the isotope-doped nano-structure includes at least two isotopes of the element, and the at least two isotopes of the element are mixed uniformly in a predetermined mass proportion. When the isotope-doped nano-structure is composed of a plurality of isotope-doped nano-structure segments, adjacent two isotope-doped nano-structure segments have different compositions. Namely, the two adjacent isotope-doped nano-structure segments can include different isotopes, or the two adjacent isotope-doped nano-structure segments also can include the same isotopes with different mass proportions.

The element can be a light element, such as carbon, boron, nitrogen or oxygen. The isotope-doped nano-structure can be a nanowire or a nanotube. The nanowire can be a carbon nanowire, a nitride nanowire, or an oxide nanowire. The nitride nanowire can be a gallium nitride nanowire, an aluminium nitride nanowire, or a silicon nitride nanowire. The oxide nanowire can be made of zinc oxide, cobalt oxide, silicon oxide, tin oxide, or ion oxide. The nanotube can be a carbon nanotube, a nitride nanotube, or an oxide nanotube. The nitride nanotube can be made of boron nitride. The oxide nanotube can be made of titanium dioxide, ferric oxide, or vanadium pentoxide.

The isotope-doped nano-structure can be made by controlling the mass proportions of its own isotopes. Further, the isotope-doped nano-structure can be made by the following steps:

providing a substrate and a reaction source having at least two kinds of isotopes of an element;

placing the substrate into a reaction chamber; and introducing the reaction source having at least two kinds of isotopes into the reaction chamber simultaneously, to grow at least one isotope-doped nano-structure segment having at least two isotopes of the element being mixed uniformly in a predetermined mass proportion on the substrate via a chemical vapor deposition method.

The reaction source can include at least two kinds of reaction gases, and each kind of reaction gases comprises a unique kind of isotope of the element. The reaction source introduced into the reaction chamber can be a premixed reaction gas, and the premixed reaction gas comprises at least two kinds of isotopes of the element with the predetermined mass proportion. The reaction source introduced into the reaction chamber also can be formed by simultaneously introducing the at least two kinds of reaction gases into the reaction chamber.

The reaction source is selected according to the isotope-doped nano-structure. For example, when the isotope-doped nano-structure is a nitrogen isotope-doped gallium nitride nanowire, the reaction source can include nitrogen source gases and a gallium source. Specifically, when the gallium nitride nanowire is composed of a gallium nitride nanowire segment, then the gallium nitride nanowire segment has two kinds of nitrogen isotopes. The gallium nitride nanowire can be formed by controlling the nitrogen source gas having a predetermined mass proportion of the two kinds of nitrogen isotopes, which reacts with the gallium source simultaneously under a catalyst. The nitrogen source gas can be gaseous ammonia, nitrogen gas, or other gaseous materials having nitrogen.

It is understood that a nitrogen isotope-doped boron nitride nanotube can be made by adjusting a nitrogen source gas having given mass proportions of nitrogen isotopes according to a predetermined sequence, and make the nitrogen source gas with a boron source in the predetermined sequence.

It is understood that an oxygen source gas can be made to have a given mass proportion of oxygen isotopes, and it can react with a zinc source, thereby, forming an isotope-doped zinc oxide nanowire.

EXAMPLE 1

Referring to FIG. 1, an isotope-doped carbon nanotube 10 of one embodiment is provided. The isotope-doped carbon nanotube 10 includes a carbon nanotube segment, the carbon nanotube segment can be composed of at least two kinds of carbon isotopes, and the at least two kinds of carbon isotopes can be mixed in a predetermined mass proportion. A length of the isotope-doped carbon nanotube 10 can be in a range of about 10 microns to about 1000 microns, and can be selected as desired. The carbon isotope can be a carbon-12 isotope, a carbon-13 isotope, or a carbon-14 isotope. In one embodiment, the isotope-doped carbon nanotube 10 consists of carbon-12 isotopes, carbon-13 isotopes, and carbon-14 isotopes at a given mass proportion of 7.2:6.5:5.6, the length of the isotope-doped carbon nanotube 10 is about 10 microns to about 50 microns, and a diameter of the isotope-doped carbon nanotube 10 is about 0.5 nanometers to about 50 nanometers.

Figure 2:
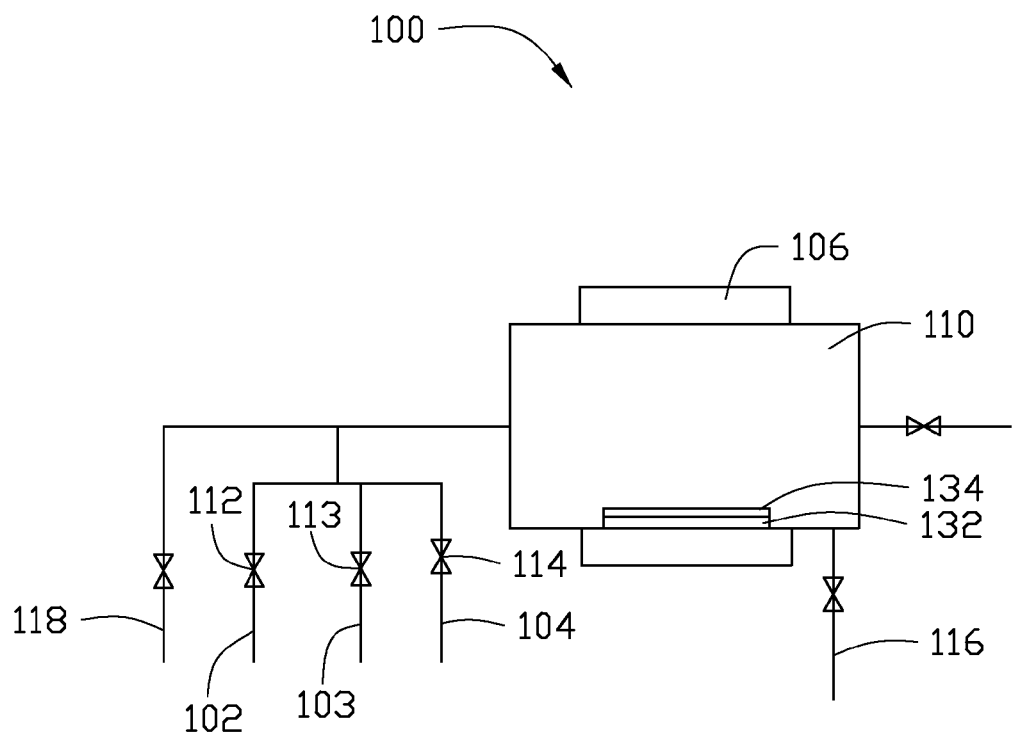
FIG. 2 is a schematic diagram of an apparatus used to form the isotope-doped carbon nanotube of FIG. 1.

A method for forming a plurality of the carbon nanotubes 10 involves chemical vapor deposition. Referring to FIG. 2, the chemical vapor deposition method includes the following steps:

(S11) providing a chemical vapor deposition device 100, a carbon source gas including three kinds of carbon isotopes, and a substrate 132 with a catalyst layer 134 deposited thereon;

(S12) placing the substrate 132 into the chemical vapor deposition device 100; and (S13) introducing the carbon source gas with the three kinds of carbon isotopes at a given mass proportion into the chemical vapor deposition device 100 simultaneously, to form the isotope-doped carbon nanotubes 10.

In step (S11), the chemical vapor deposition device 100 includes a reaction chamber 110, a reaction furnace 106 for heating the reaction chamber 110, a protective gas supply conduit 118, three carbon source gas supply pipes 102, 103, 104, and a vent-pipe 116. The carbon source gas supply pipe 102 has a valve 112. The carbon source gas supply pipe 103 has a valve 113. The carbon source gas supply pipe 104 has a valve 114.

The carbon source gas includes three kinds of ethylene gas, and each kind of ethylene gas has a unique kind of carbon isotope. The carbon isotopes are a carbon-12 isotope, a carbon-13 isotope and a carbon-14 isotope. It is understood that the ethylene gas can instead be methane, ethyne, propadiene or other carbon hydrogen compounds.

The catalyst layer 134 can be made of iron, nickel, cobalt, or other suitable catalyst, and can be formed by means of, e.g., a chemical vapor deposition method, a thermal deposition method, an electron-beam deposition method, or a sputtering method. In one embodiment, the catalyst layer 134 is about a 5-nanometer thick iron film.

In step (S13), the reaction chamber 110 is vacuumized via the vent-pipe 116. A protective gas under a pressure of 1 atmosphere is introduced into the reaction chamber 110 through the protective gas supply conduit 118, at the same time, the reaction chamber 110 is heated to 700° C. using a reaction furnace 106 disposed therearound. The valves 112, 113,114 are opened simultaneously and the ethylene gas having carbon-12 isotopes is introduced into the reaction chamber 110 through the carbon source gas supply pipe 102 at a flow rate of about 120 sccm (standard cubic centimeters per minute); the ethylene gas having carbon-13 isotopes is introduced into the reaction chamber 110 through the carbon source gas supply pipe 103 at a flow rate of about 100 sccm; the ethylene gas having carbon-14 isotopes is introduced into the reaction chamber 110 through the carbon source gas supply pipe 104 at a flow rate of about 80 sccm. Thus, the isotope-doped carbon nanotube 10 having carbon-12 isotopes, carbon-13 isotopes, and carbon-14 isotopes is formed on the catalyst layer 134. The protective gas can be helium, nitrogen, argon or hydrogen. In one embodiment, the protective gas is argon.

It is understood the carbon source gas can be a premixed carbon hydrogen gas having three carbon isotopes with a given mass proportion. The isotope-doped carbon nanotube 10 can be formed by introducing the premixed carbon hydrogen gas into the reaction chamber 110 through a carbon source gas supply pipe. In one embodiment, the isotope-doped carbon nanotube 10 is made by introducing a premixed ethylene gas having carbon-12 isotopes, carbon-13 isotopes, carbon-14 isotopes with the mass proportion of 7.2:6.5:5.6, into the reaction chamber 110 through the carbon source gas supply pipe 102.

EXAMPLE 2

Figure 3:
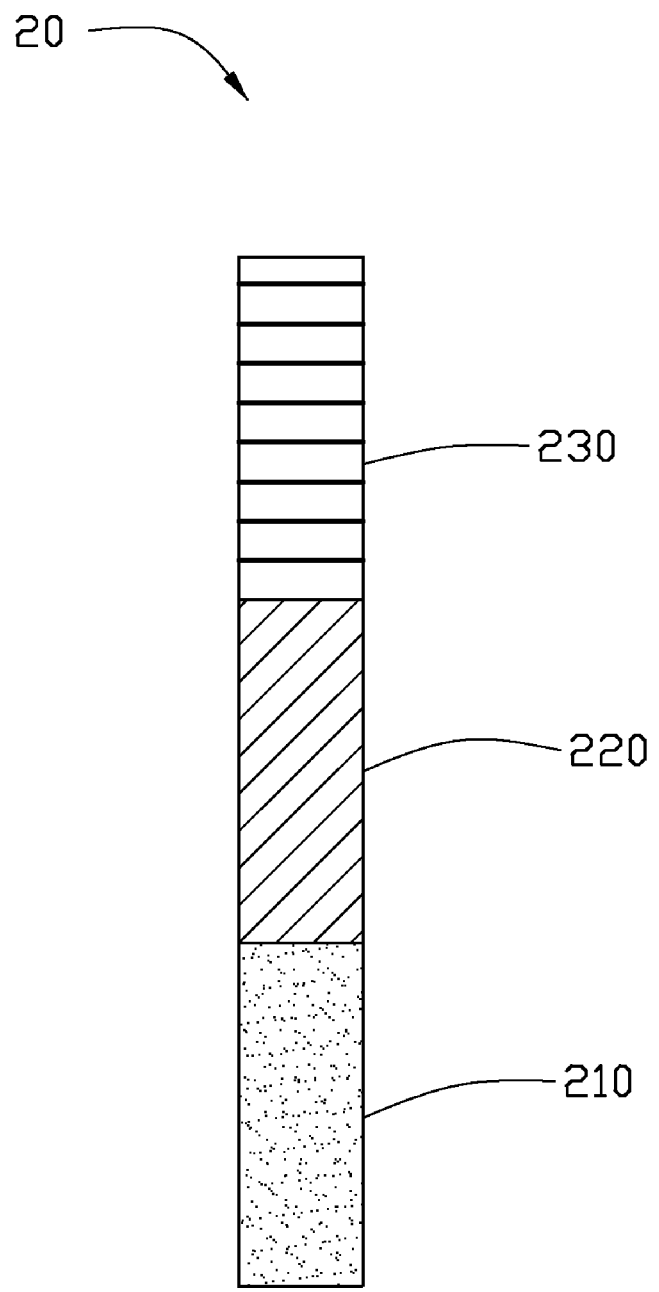
FIG. 3 is a schematic view of one embodiment of an isotope-doped carbon nanotube.

Referring to FIG. 3, an isotope-doped carbon nanotube 20 of one embodiment is provided. The isotope-doped carbon nanotube 20 includes a first kind of carbon nanotube segment 210, a second kind of carbon nanotube segment 220 growing on the first kind of carbon nanotube segment 210, and a third kind of carbon nanotube segment 230 growing on the second kind of carbon nanotube segment 230. The first kind of carbon nanotube segment 210 consists of carbon-12 isotopes and carbon-14 isotopes, and carbon-12 isotopes and carbon-14 isotopes are mixed evenly in the first kind of carbon nanotube segment 210 with a mass proportion of about 8:7. The second kind of carbon nanotube segment 220 consists of carbon-12 isotopes, carbon-13 isotopes, and carbon-14 isotopes at a mass proportion of about 8:8:7. The third kind of carbon nanotube segment 230 consists of carbon-12 isotopes. The isotope-doped carbon nanotube 20 is about 30 microns to about 50 microns in length.

It is understood that the composition of each carbon nanotube segment of the isotope-doped carbon nanotube is not limited to that described above, and can be selected as desired, such as the second kind of carbon nanotube segment 220 can consist of carbon-13 isotopes and carbon-14 isotopes at a mass proportion of about 8:7.

Referring to FIG. 2, a method for making the isotope-doped carbon nanotubes 20 is provided. The method includes the following steps:

(S21) providing the chemical vapor deposition device 100, a carbon source including three kinds of carbon source gas, and the substrate 132 with the catalyst layer 134 deposited thereon, wherein each kind of carbon source gas having a unique kind of carbon isotope;

(S22) placing the substrate 132 into the chemical vapor deposition device 100; and (S23) changing proportions of carbon source gases introduced into the chemical vapor deposition device 100 according to a predetermined sequence, to grow a variety of carbon nanotube segments, thereby forming the isotope-doped carbon nanotubes 20.

Step (S23) includes the following steps:

(S231) vacuumizing the reaction chamber 110 via the vent-pipe 116, introducing argon gas under a pressure of 1 atmosphere into the reaction chamber 110 through the protective gas supply conduit 118, and heating the reaction chamber 110 up to 700° C. using the reaction furnace 106;

(S232) opening the valves 112 and 114, and introducing an ethylene gas having carbon-12 isotopes into the reaction chamber 110 through the carbon source gas supply pipe 102 at a flow rate of about 120 sccm; simultaneously, an ethylene gas having carbon-14 isotopes is introduced into the reaction chamber 110 through the carbon source gas supply pipe 104 at a flow rate of about 90 sccm; whereby the first kind of carbon nanotube segments 210 having carbon-12 isotopes and carbon-14 isotopes at the mass proportion of about 8:7 are formed on the substrate 132;

(S233) after a first given time, when the first kind of carbon nanotube segments 210 have reached a first predetermined length, opening the valve 113 and introducing an ethylene gas having carbon-13 isotopes into the reaction chamber 110, through the carbon source gas supply pipe 103 at a flow rate of about 110 sccm, whereby the second kind of carbon nanotube segments 220 having carbon-12 isotopes, carbon-13 isotopes, and carbon-14 isotopes with the mass proportion of about 8:8:7 are formed on the first kind of carbon nanotube segments 210;

(S234) after a second given time, when the second kind of carbon nanotube segments 220 have reached a second predetermined length, closing the valve 113 and 114 to stop the flow of ethylene gas having carbon-13 isotopes and carbon-14 isotopes, the ethylene gas having carbon-12 isotopes still being introduced into the reaction chamber 110, whereby the third kind of carbon nanotube segments 230 having carbon-12 isotopes are formed on the second kind of carbon nanotube segments 220; and (S235) after a third given time, when the third kind of carbon nanotube segments 230 have reached a third predetermined length, closing the valves 112, 113 and 114 to stop the flow of ethylene gas having carbon-12 isotopes, carbon-13 isotopes, and carbon-14 isotopes, cooling the reaction chamber 110 down to room temperature, thereby leaving the isotope-doped carbon nanotubes 20 formed on the substrate 132.

It is understood that the method for forming the isotope-doped carbon nanotubes 20 can include the following steps:

(a) providing the chemical vapor deposition device 100, three carbon sources, and the substrate 132 with the catalyst layer 134 deposited thereon;

(b) placing the substrate 132 into the chemical vapor deposition device 100; and (c) introducing the three carbon source gases into the chemical vapor deposition device 100 according to a predetermined sequence, to grow first, second, and third kinds of carbon nanotube segments, thereby forming the isotope-doped carbon nanotube 20 on the substrate 132.

In step (a), the first carbon source is a first premixed carbon source gas. The first premixed carbon source gas includes a mixed carbon source gas having carbon-12 isotopes and carbon-14 isotopes. A mass proportion of the carbon-12 isotopes and carbon-14 isotopes is about 8:7. The second carbon source gas is a second premixed carbon source gas. The second premixed carbon source gas includes a mixed carbon source gas having carbon-12 isotopes, carbon-13 isotopes, and carbon-14 isotopes. A mass proportion of the carbon-12 isotopes, carbon-13 isotopes, and carbon-14 isotopes is about 8:8:7. The third carbon source gas is a carbon source gas having carbon-12 isotopes.

EXAMPLE 3

Figure 4:
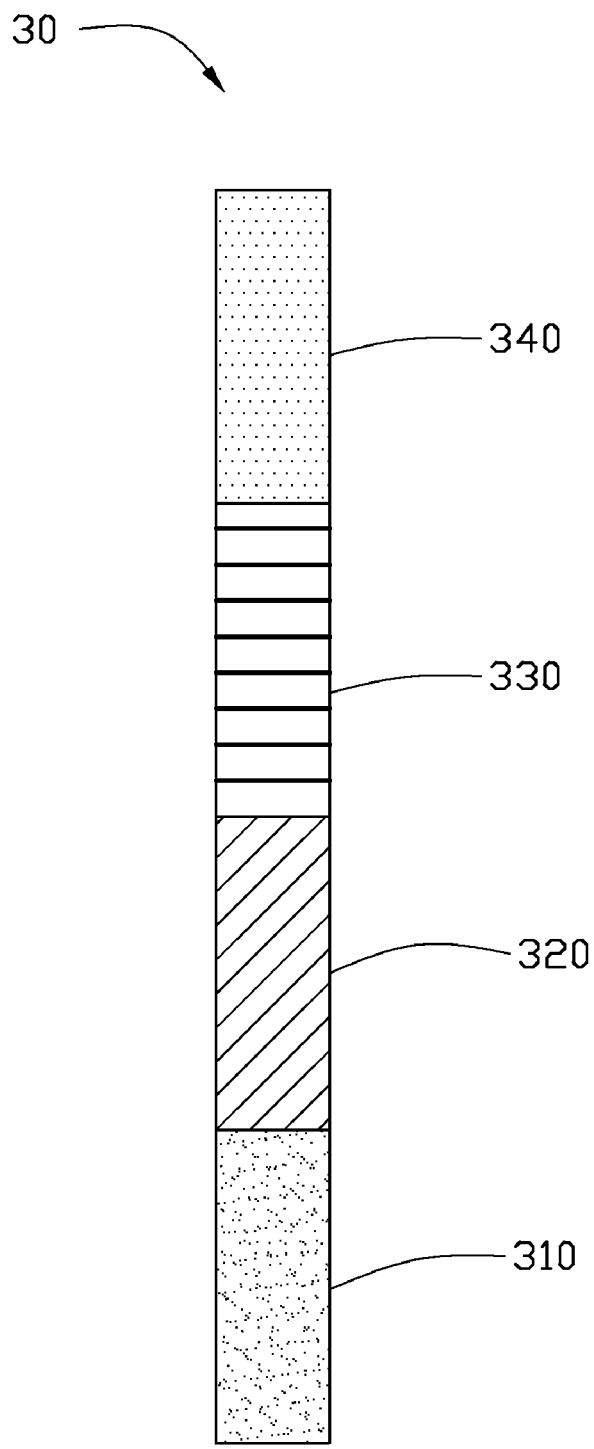
FIG. 4 is a schematic view of one embodiment of an isotope-doped carbon nanotube.

Referring to FIG. 4, an isotope-doped carbon nanotube 30 of one embodiment is provided. The isotope-doped carbon nanotube 30 includes a first kind of carbon nanotube segment 310, a second kind of carbon nanotube segment 320 formed on the first kind of carbon nanotube segment 310, a third kind of carbon nanotube segment 330 formed on the second kind of carbon nanotube segment 320, and a fourth kind of carbon nanotube segment 340 grown on the third kind of carbon nanotube segment 330. The first kind of carbon nanotube segment 310 consists of carbon-12 isotopes, carbon-13 isotopes, and carbon-14 isotopes at a mass proportion about 7:7:6.5. The second kind of carbon nanotube segment 320 consists of carbon-12 isotopes, carbon-13 isotopes and carbon-14 isotopes at a mass proportion about 7.2:6.5:5.6. The third kind of carbon nanotube segment 330 consists of carbon-12 isotopes, carbon-13 isotopes, and carbon-14 isotopes at a mass proportion about 5.5:6.5:7. The fourth kind of carbon nanotube segment 340 consists of carbon-13 isotopes and carbon-14 isotopes at a mass proportion about 1:1. The isotope-doped carbon nanotube 30 is about 50 microns to about 100 microns in length.

The method for making the isotope-doped carbon nanotube 30 can be the same as that of the isotope-doped carbon nanotube 20. Namely, the isotope-doped carbon nanotube 30 can be made by changing the mass proportions of carbon source gases introduced into the chemical vapor deposition device 100 according to a predetermined sequence, to grow the four kinds of carbon nanotube segments. Further, the step of changing the mass proportions of carbon source gases introduced into the chemical vapor deposition device 100 can be executed by controlling the flow rate of carbon source gases introduced into the chemical vapor deposition device 100.

Referring to FIG. 5, a labeling method using isotope-doped nano-structures is provided. The method includes the following steps:

providing a plurality of different types of unlabeled structures, and a plurality of different kinds of isotope-doped nano-structures of an element having certain Raman spectrum eigenvalues, wherein, each kind of isotope-doped nano-structure includes at least one isotope-doped nano-structure segment having at least two isotopes of the element, and the at least two isotopes of the element are mixed uniformly in a predetermined mass proportion;

implanting one kind of the isotope-doped nano-structures of the element in one type of the unlabeled structures;

measuring the Raman spectrum eigenvalues of isotope-doped nano-structures of the element planted in the unlabeled structures via Raman spectroscopy; and distinguishing the unlabeled structures in accordance with the measured Raman spectrum eigenvalues.

The unlabeled structures can have active groups. The active groups can be hydroxyl groups, carboxyl group, amino group, acyl group, or nitro groups. The unlabeled structures can be DNAs, proteins, glucoses, gluconic acids, starches, biotin enzymes, sorbitols, or organic amines. The characteristics of the unlabeled structures cannot be affected by the planted isotope-doped nano-structures.

Referring to FIG. 1, FIG. 3 and FIG. 4, in one embodiment, a labeling method using the carbon nanotubes 10, 20, and 30 to label glucoses, gluconic acids, and sorbitols is provided.

Specifically, (W10) providing three kinds of unlabeled structures, the isotope-doped carbon nanotubes 10, 20, and 30, wherein the three kinds of unlabeled structures are glucoses, gluconic acids, and sorbitols, the Raman spectrum eigenvalue of the carbon nanotubes 10 is L1, the Raman spectrum eigenvalue of the carbon nanotubes 20 is L2, and the Raman spectrum eigenvalue of the carbon nanotubes 30 is L3;

(W20) implanting the carbon nanotubes 10 in the glucoses, the carbon nanotubes 20 in the gluconics acids, and the carbon nanotubes 30 in the sorbitols;

(W30) measuring the Raman spectrum eigenvalues of the implanted carbon nanotubes in the gluconics acids, the glucoses, and the sorbitols by Raman spectroscopy, thereby obtaining the Raman spectrum eigenvalues of the carbon nanotubes, wherein, the measured Raman spectrum eigenvalues are L1, L2, L3; and (W40) distinguishing the unlabeled structures of glucoses, gluconic acids, and sorbitols according to the measured Raman spectrum eigenvalues.

As described above, each of the isotope-doped nano-structures of an element includes at least one isotope-doped nano-structure segment having at least two isotopes of the element, and the at least two isotopes of the element are uniformly mixed therein in a predetermined mass proportion. The isotope-doped nano-structures of the element vary with the varieties of the isotopes and the proportions of the isotopes. Thus, the disclosure can provide a variety of isotope-doped nano-structures of an element. The isotope-doped nano-structures of an element can be used to label a variety of unlabeled structures at the same time, and thus process a greater number of the unlabeled structures, which is conducive to researching the properties of the variety of unlabeled structures, and the changes in the unlabeled structures under different conditions.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for forming an isotope-doped nano-structure of an element, comprising the steps of:
   (a) providing a substrate and placing the substrate into a reaction chamber;
   (b) introducing a reaction source having at least two isotopes of the element into the reaction chamber simultaneously, maintaining the at least two isotopes of the element at a predetermined mass proportion and being mixed uniformly; and
   (c) growing at least one isotope-doped nano-structure segment having the at least two isotopes of the element being mixed uniformly at a predetermined mass proportion on the substrate via a chemical vapor deposition method, wherein step (c) is performed after step (b).

2. The method of claim 1, wherein the reaction source comprises at least two kinds of reaction gases, and each of the at least two kinds of reaction gases comprises a unique kind of isotope of the element.

3. The method of claim 2, wherein the step (b) is executed by changing proportions of reaction gases introduced in the reaction chamber according to a predetermined sequence, to grow a plurality of isotope-doped nano-structure segments for given times according to the predetermined sequence, thereby forming the isotope-doped nano-structure of the element.

4. The method of claim 1, wherein the reaction source comprises at least one premixed reaction gas having the at least two isotopes of the element at the predetermined mass proportion.

5. The method of claim 4, wherein the step (b) is executed by introducing the at least one premixed reaction gas into the reaction chamber according to a predetermined sequence; and growing a plurality of isotope-doped nano-structure segments for given times according to the predetermined sequence, thereby forming the isotope-doped nano-structure of the element.

6. The method of claim 1, wherein the isotope-doped nano-structure is a carbon nanotube, the reaction source is a carbon source, the carbon source comprises at least two kinds of carbon source gases, and each of the at least two kinds of carbon source gases has a unique kind of carbon isotope.

7. A labeling method using isotope-doped nano-structures, comprising the steps of:
   providing a substrate and placing the substrate into a reaction chamber;
   introducing a reaction source having at least two isotopes of the element into the reaction chamber simultaneously, maintaining the at least two isotopes of the element at a predetermined mass proportion and being mixed uniformly;
   growing a plurality of different kinds of isotope-doped nano-structures of an element having certain Raman spectrum eigenvalues, each kind of isotope-doped nano-structure comprising at least one isotope-doped nano-structure segment having at least two isotopes of the element, and the at least two isotopes of the element being mixed uniformly in a predetermined mass proportion;
   providing a plurality of different types of unlabeled structures;
   implanting one kind of the isotope-doped nano-structures of the element in one type of the unlabeled structures;
   measuring the Raman spectrum eigenvalues of isotope-doped nano-structures of the element planted in the unlabeled structures via Raman spectroscopy; and
   distinguishing the unlabeled structures in accordance with the measured Raman spectrum eigenvalues.

8. The method of claim 7, wherein each type of unlabeled nano-structure comprises an active group.

9. The method of claim 8, wherein the active group is selected from the group consisting of a hydroxyl group, a carboxyl group, an amino group, an acyl group, and a nitro group.

10. The method of claim 8, wherein the unlabeled structures are selected from the group consisting of DNAs, proteins, glucoses, gluconic acids, starches, biotin enzymes, sorbitols, and organic amines.

11. The method of claim 7, wherein the isotope-doped nano-structure comprises at least two isotope-doped nano-structure segments having the at least two isotopes of the element, and adjacent two isotope-doped nano-structure segments have different compositions.

12. The method of claim 11, wherein the adjacent two isotope-doped nano-structure segments comprise different isotopes of the element.

13. The method of claim 11, wherein the adjacent two isotope-doped nano-structure segments comprise the same isotopes of the element, and predetermined mass proportions of the isotopes are different.

14. A method for forming an isotope-doped nano-structure of an element, comprising the steps of:
   (a) providing a substrate and placing the substrate into a reaction chamber;
   (b) mixing at least two reaction sources to obtain a reaction source mixture having at least two isotopes of the element at a predetermined mass proportion and mixed uniformly; and
   (c) introducing the reaction source mixture into the reaction chamber, and growing at least one isotope-doped nano-structure segment having the at least two isotopes of the element being mixed uniformly at a predetermined mass proportion on the substrate via a chemical vapor deposition method.

* * * * *